United States Patent
Dellinger et al.

(10) Patent No.: US 7,572,907 B2
(45) Date of Patent: Aug. 11, 2009

(54) METHODS AND COMPOUNDS FOR POLYNUCLEOTIDE SYNTHESIS

(75) Inventors: Douglas J. Dellinger, Boulder, CO (US); Geraldine Dellinger, Boulder, CO (US); Marvin H. Caruthers, Boulder, CO (US); Zoltan Kupihar, Boulder, CO (US)

(73) Assignees: Agilent Technologies, Inc., Santa Clara, CA (US); The Regents of the University of Colorado, Denver, CO (US)

( * ) Notice: Subject to any disclaimer, the term of this patent is extended or adjusted under 35 U.S.C. 154(b) by 635 days.

(21) Appl. No.: 11/118,599

(22) Filed: Apr. 29, 2005

(65) Prior Publication Data

US 2006/0247430 A1    Nov. 2, 2006

(51) Int. Cl.
*C07H 21/00*    (2006.01)
(52) U.S. Cl. .................. 536/25.3; 536/25.33
(58) Field of Classification Search ........................ None
See application file for complete search history.

(56) References Cited

OTHER PUBLICATIONS

Sierzchala et al. "Solid-Phase Oligodeoxynucleotide Synthesis: A two Step Cycle Using Peroxy Anion Deprotection", Journal of American Chemical Society, 125, 13427-13441, 2003.*
Europeán Search Report dated Jul. 27, 2006, 5 pages.
Sierzchala Agnieszka B. et al., Solid-phase oligodeoxynucleotide synthesis: A two-step cycle using peroxy anion deprotection: Journal of the American Chemical Society, vol. 125, No. 44, Nov. 5, 2003 pp. 13427-13441.
Beaucage S. L., et al. "Advances in the Synthesis of Oligonucleotides by the Phosphoramidite Approach" Tetrahedron, Elsevier Science Publishers, Amsterdam, NL, vol. 48, No. 12, 1992, pp. 2223-2311.
Seio, K, et al., "Syntesis of pentathymidylate using a 4-monomethoxytritylthio (MMTrS) group as a 5'-hydroxyl protecting group: toward oligonucleotide synthesis without acid treatment" Tetrahedron Letters, Elsevier, Amsterdam, NL, vol. 42, No. 49, Dec. 3, 2001, pp. 8657-8660.

* cited by examiner

*Primary Examiner*—Traviss C McIntosh, III

(57) ABSTRACT

Methods of forming polynucleotides are disclosed.

9 Claims, 3 Drawing Sheets

METHODS AND COMPOUNDS FOR POLYNUCLEOTIDE SYNTHESIS

STATEMENT REGARDING FEDERALLY SPONSORED RESEARCH OR DEVELOPMENT

The U.S. government may have a paid-up license in this invention and the right in limited circumstances to require the patent owner to license others on reasonable terms as provided for by the terms of MDA CONTRACT N39998-01-9-7068 awarded by the DARPA of the U.S. Government.

BACKGROUND

Much interest has been focused on reactions for coupling nucleotides to form polynucleotide chains, and various chemical schemes have been described for the synthesis of polynucleotides. Typically these methods use a nucleoside reagent of the formula:

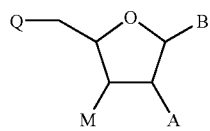

(I)

in which:

A represents H, OH, halogen, or an optionally protected hydroxyl group;

B is a purine or pyrimidine base whose exocyclic amine functional group is optionally protected;

one of M or Q is a conventional protective group for the 3' or 5'—OH functional group while the other is:

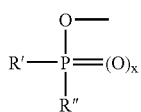

(II)

where x may be 0 or 1, provided that:

a) when x=1:

R' represents H and R" represents a negatively charged oxygen atom; or

R' is an oxygen atom and R" represents either an oxygen atom or an oxygen atom carrying a protecting group; and b) when x=0, R' is an oxygen atom carrying a protecting group and R" is either a hydrogen or a di-substituted amine group.

When x is equal to 1, R' is an oxygen atom and R" is an oxygen atom, the method is in this case the so-called phosphodiester method; when R" is an oxygen atom carrying a protecting group, the method is in this case the so-called phosphotriester method.

When x is equal to 1, R' is a hydrogen atom and R" is a negatively charged oxygen atom, the method is known as the H-phosphonate method.

When x is equal to 0, R' is an oxygen atom carrying a protecting group and R" is a halogen, the method is known as the phosphite method, and when R" is a leaving group of the disubstituted amine type, the method is known as the phosphoramidite method.

The conventional sequence used to prepare an oligonucleotide using reagents of the type of formula (I), basically follows four separate steps: (a) coupling a selected nucleoside which also has a protected hydroxy group, through a phosphite linkage to a functionalized support in the first iteration, or a nucleoside bound to the substrate (i.e., the nucleoside-modified substrate) in subsequent iterations; (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate-bound nucleoside coupled in step (a), to generate a reactive site for the next cycle of these steps. The functionalized support (in the first cycle) or deprotected coupled nucleoside (in subsequent cycles) provides a substrate-bound moiety with a linking group for forming the phosphite linkage with a next nucleoside to be coupled in step (a). Final deprotection of nucleoside bases can be accomplished using alkaline conditions such as ammonium hydroxide, methyl amine, ethanolamine, or others, in a known manner.

The foregoing methods of preparing polynucleotides are well known and described in detail, for example, in Caruthers, Science 230: 281-285, 1985; Itakura et al., Ann. Rev. Biochem. 53: 323-356; Hunkapillar et al., Nature 310: 105-110, 1984; and in "Synthesis of Oligonucleotide Derivatives in Design and Targeted Reaction of Oligonucleotide Derivatives", CRC Press, Boca Raton, Fla. pages 100 et seq., U.S. Pat. Nos. 4,415,732, 4,458,066, 4,500,707, 5,153,319, 5,869, 643, EP 0294196, and elsewhere. The phosphoramidite and phosphite triester approaches are most broadly used, but other approaches include the phosphodiester approach, the phosphotriester approach and the H-phosphonate approach. Such approaches are described in Beaucage et al., Tetrahedron (1992) 12:2223-2311. A more recent approach for synthesis of polynucleotides is described in U.S. Pat. No. 6,222,030 B1 to Dellinger et al, Issued Apr. 24, 2001.

In the typical phosphoramidite method of solid phase oligonucleotide synthesis, the synthesis typically proceeds in the 3' to 5' direction (referring to the sugar component of the added nucleoside), although the synthesis may easily be conducted in the reverse direction. The added nucleoside generally has a dimethoxytrityl protecting group on its 5' hydroxyl and a phosphoramidite functionality on its 3' hydroxyl position. Beaucage et al. (1981) Tetrahedron Lett. 22:1859. See FIG. 1 for a schematic representation of this technology. In FIG. 1 "B" represents a purine or pyrimidine base, "DMT" represents dimethoxytrityl protecting group and "iPr" represents isopropyl. In the first step of the synthesis cycle, the "coupling" step, the 5' end of the growing chain is coupled with the 3' phosphoramidite of the incoming monomer to form a phosphite triester intermediate (the 5' hydroxyl protecting group prevents more than one monomer per synthesis cycle from attaching to the growing chain). Matteucci et al. (1981) J. Am. Chem. Soc. 103:3185. Next, the optional "capping reaction" is used to stop the synthesis on any chains having an unreacted 5' hydroxyl, which would be one nucleotide short at the end of synthesis. The "capping reaction" has the added benefit of cleaving coupling products from the heterobases, such as O-6 adducts on guanosine, prior to the oxidation step. The phosphite triester intermediate is subjected to oxidation (the "oxidation" step) after each coupling reaction to yield a more stable phosphotriester intermediate. Without oxidation, the unstable phosphite triester linkage would cleave under the acidic conditions of subsequent synthesis steps. Letsinger et al. (1976) J. Am. Chem. Soc. 98:3655. Removal of the 5' protecting group of the newly added monomer (the "deprotection" step) is typically accomplished by reaction with acidic solution to yield a free 5' hydroxyl group, which can be coupled to the next protected nucleoside phosphoramidite. This process is repeated for each monomer added until the desired sequence is synthesized.

According to some protocols, the synthesis cycle of couple, cap, oxidize, and deprotect is shortened by omitting the capping step or by taking the oxidation step 'outside' of the cycle and performing a single oxidation reaction on the completed chain. For example, oligonucleotide synthesis according to H-phosphonate protocols will permit a single oxidation step at the conclusion of the synthesis cycles. However, coupling yields are less efficient than those for phosphoramidite chemistry and oxidation requires longer times and harsher reagents than amidite chemistry.

Conventional synthesis protocols of oligonucleotides are not without disadvantages. For example, cleavage of the DMT protecting group under acidic conditions gives rise to the resonance-stabilized and long-lived bis(p-anisyl)phenylmethyl carbocation. Gilham et al. (1959) J. Am. Chem. Soc. 81:4647. Protection and deprotection of hydroxyl groups with DMT are thus readily reversible reactions, resulting in incomplete reactions during oligonucleotide synthesis giving rise to sequence deletions and a lower yield than might otherwise be obtained. To circumvent such problems, large excesses of acid are used with DMT to achieve quantitative deprotection. However, the repeated exposure of DNA sequences to acids gives rise to acid catalyzed removal of the heterobases from the sugar ring. Heterobase removal is most facile on the purine bases, adenosine, and guanosine; resulting in depurination, however all heterobases and modified heterobases can be susceptible to acid catalyzed removal. As bed volume of the polymer is increased in larger scale synthesis, increasingly greater quantities of acid are required. The acid-catalyzed depurination that occurs during the synthesis of oligodeoxyribonucleotides is thus increased by the scale of synthesis. Caruthers et al., in Genetic Engineering: Principles and Methods, J. K. Setlow et al., Eds. (New York: Plenum Press, 1982). Solvent use in larger scale synthesis becomes increasingly prohibitive as well, as more washing is required. In particular, the reagents used in the coupling step typically are highly susceptible to hydrolysis, which requires dry solvents, further increasing the cost of solvents.

SUMMARY

Briefly described, embodiments of this disclosure include method of forming polynucleotides. One exemplary method, among others, includes providing a structure X selected from structure C' and O' illustrated herein; where R1 is selected from substituted carbonyls, substituted silanes and functional groups, wherein the functional group is selected from carbonate, ester, amide, carbamate, silane, siloxane, orthoester, acetal, and ketal; R2 is selected from benzyl, substituted benzyl, phenyl, substituted phenyl, tertiary alkyl, substituted tertiary alkyl; B comprises purine and pyrimidine bases and analogs thereof; wherein n is from 1 to 350; and wherein ● is a substrate; and oxidizing and deprotecting structure X simultaneously, wherein the aqueous buffer solution is an oxidant and a nucleophile at a pH of about 6 to 10.

Additional objects, advantages, and novel features of this disclosure shall be set forth in part in the descriptions and examples that follow and in part will become apparent to those skilled in the art upon examination of the following specifications or may be learned by the practice of the disclosure. The objects and advantages of the disclosure may be realized and attained by means of the instruments, combinations, compositions, and methods particularly pointed out in the appended claims.

BRIEF DESCRIPTION OF THE DRAWINGS

Reference is now made to the following drawings. Note that the components in the drawings are not necessarily to scale.

DETAILED DESCRIPTION

Figure 1:
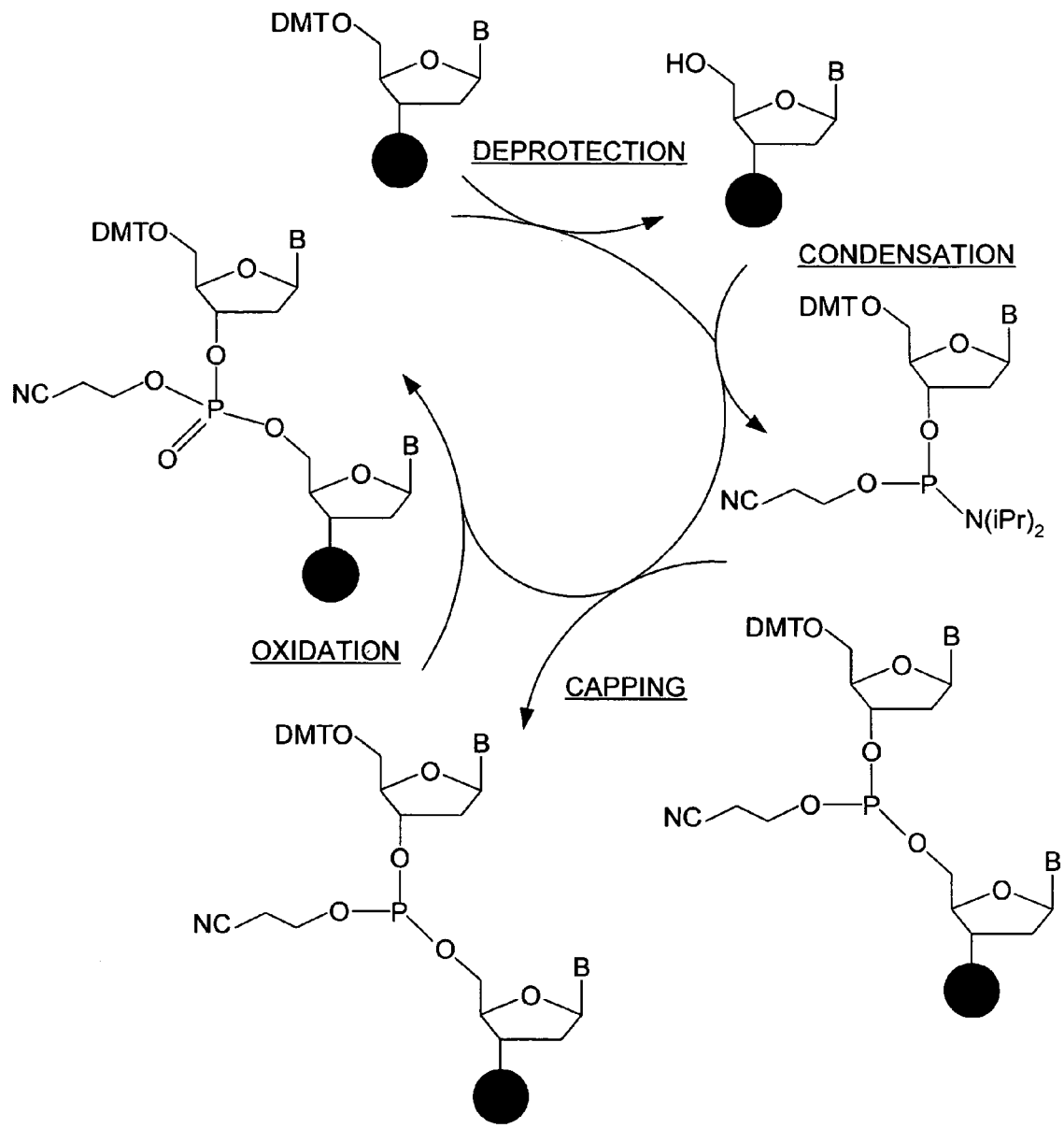
FIG. 1 schematically illustrates a prior art multi-step polynucleotide/oligonucleotide synthesis method.

Embodiments of the present disclosure will employ, unless otherwise indicated, conventional techniques of synthetic organic chemistry, biochemistry, molecular biology, and the like, which are within the skill of one in the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that unless otherwise indicated the present disclosure is not limited to particular materials, reagents, reaction materials, manufacturing processes, or the like, as such may vary. It is also to be understood that the terminology used herein is for purposes of describing particular embodiments only, and is not intended to be limiting. It is also possible in the present disclosure that steps may be executed in different sequence where this is logically possible.

It must be noted that, as used in the specification and the appended claims, the singular forms "a," "an" and "the" include plural referents unless the context clearly dictates otherwise. Thus, for example, reference to "a support" includes a plurality of supports. In this specification and in the claims that follow, reference will be made to a number of terms that shall be defined to have the following meanings, unless a contrary intention is apparent.

As used herein, polynucleotides include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base.

A "nucleotide" refers to a sub-unit of a nucleic acid (whether DNA or RNA or analogue thereof) which includes a phosphate group, a sugar group and a nitrogen containing base, as well as analogs of such sub-units.

A "nucleoside" references a nucleic acid subunit including a sugar group and a nitrogen containing base. It should be noted that the term "nucleotide" is used herein to describe embodiments of the disclosure, but that one skilled in the art would understand that the term "nucleoside" and "nucleotide" are interchangable in most instances. One skilled in the art would have the understanding that additional modification to the nucleoside may be necessary and one skilled in the art has such knowledge.

A "nucleoside moiety" refers to a molecule having a sugar group and a nitrogen containing base (as in a nucleoside) as a portion of a larger molecule, such as in a polynucleotide, oligonucleotide, or nucleoside phosphoramidite.

A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer.

A "polynucleotide intermediate" references a molecule occurring between steps in chemical synthesis of a polynucleotide, where the polynucleotide intermediate is subjected to further reactions to get the intended final product (e.g., a phosphite intermediate, which is oxidized to a phosphate in a later step in the synthesis), or a protected polynucleotide, which is then deprotected.

An "oligonucleotide" generally refers to a nucleotide multimer of about 2 to 100 nucleotides in length, while a "polynucleotide" includes a nucleotide multimer having any number of nucleotides greater than 1.

It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., diaminopurine and its derativites, inosine and its derativites, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group.

An "array", unless a contrary intention appears, includes any one, two, or three dimensional arrangement of addressable regions bearing a particular chemical moiety or moieties (for example, polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). While probes and targets of the present disclosure will typically be single-stranded, this is not essential. An "array layout" refers to one or more characteristics of the array, such as feature positioning, feature size, and some indication of a moiety at a given location. "Hybridizing" and "binding", with respect to polynucleotides, are used interchangeably.

A "group" includes both substituted and unsubstituted forms. Typical substituents include one or more lower alkyl, any halogen, hydroxy, or aryl, or optionally substituted on one or more available carbon atoms with a nonhydrocarbyl substituent such as cyano, nitro, halogen, hydroxyl, or the like. Any substituents are typically chosen so as not to substantially adversely affect reaction yield (for example, not lower it by more than 20% (or 10%, or 5% or 1%) of the yield otherwise obtained without a particular substituent or substituent combination). An "acetic acid" includes substituted acetic acids such as di-chloroacetic acid (DCA) or tri-chloroacetic acid (TCA).

A "phospho" group includes a phosphodiester, phosphotriester, and H-phosphonate groups. In the case of either a phospho or phosphite group, a chemical moiety other than a substituted 5-membered furyl ring may be attached to O of the phospho or phosphite group which links between the furyl ring and the P atom.

A "protecting group" is used in the conventional chemical sense to reference a group, which reversibly renders unreactive a functional group under specified conditions of a desired reaction. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment.

A "hydroxyl protecting group" refers to a protecting group where the protected group is a hydroxyl. A "reactive-site hydroxyl" is the terminal 5'-hydroxyl during 3'-5' polynucleotide synthesis and is the 3'-hydroxyl during 5'-3' polynucleotide synthesis. An "acid labile protected hydroxyl" is a hydroxyl group protected by a protecting group that can be removed by acidic conditions. Similarly, an "acid labile protecting group" is a protecting group that can be removed by acidic conditions. Preferred protecting groups that are capable of removal under acidic conditions ("acid-labile protecting groups") include those such as tetrahydropyranyl groups, e.g., tetrahydropyran-2-yl and 4-methoxytetrahydropyran-2-yl; an arylmethyl group with n aryl groups (where n=1 to 3) and 3-n alkyl groups such as an optionally substituted trityl group, for example a monomethoxytrityl for oligoribonucleotide synthesis and a dimethoxytrityl for oligodeoxyribonucleotide synthesis; pixyl; isobutyloxycarbonyl; t-butyl; and dimethylsilyl. A trityl group is a triphenylmethyl group. Suitable protecting groups are described in "Protective Groups in Organic Synthesis" by T.W. Green, Wiley Interscience.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to eight carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl, and cyclooctyl.

The term "aryl" as used herein refers to an aromatic species containing 1 to 5 aromatic rings, either fused or linked, and either unsubstituted or substituted with 1 or more substituents typically selected from the group consisting of amino, halogen, and lower alkyl. Preferred aryl substituents contain 1 to 3 fused aromatic rings, and particularly preferred aryl substituents contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —$(CH_2)_j$—Ar wherein j is an integer in the range of 1 to 24, more typically 1 to 6, and Ar is a monocyclic aryl moiety.

Discussion

Embodiments of the present disclosure include methods for fabricating oligonucleotides and polynucleotides (hereinafter "polynucleotide"), methods of deprotecting the hydroxyl on the sugar moiety of a nucleotide and deprotecting the nascent internucleotide bond simultaneously, protecting groups for the hydroxyl group on the sugar moiety of a nucleotide, protecting groups for the nascent internucleotide bond between two nucleotides, and nucleotide compounds including protecting groups for the hydroxyl group on the sugar moiety of a nucleotide and protecting groups for the nascent internucleotide bond between two nucleotides, all of which have numerous advantages relative to prior methods such as those discussed above.

In general, the methods involve forming a target biopolymer (hereinafter "target polynucleotide") using nucleotide compounds including protecting groups for the hydroxyl group on the sugar moiety of a nucleotide and protecting groups for the nascent internucleotide bond between two nucleotides. In general, the methods involve a coupling step and a deprotection and oxidative step, where the deprotection and oxidative steps occur simultaneously. In the simultaneous deprotection and oxidative step, deprotecting the hydroxyl on the sugar moiety of the nucleotide and deprotecting the nascent internucleotide bond between two adjacent nucleotides occurs simultaneously or substantially simultaneously. In particular, the simultaneous deprotection and oxidative steps are substantially irreversible or irreversible. Substantially irreversible means at least 80% irreversible, at least 90% irreversible, and at least 95% irreversible.

In addition, the number of steps used in the methods for synthesizing the target polynucleotide is reduced relative to that shown in FIG. 1. In particular, the methods involve a two-step synthesis cycle that can be used to produce target polynucleotides in either the 5' to 3' direction or the 3' to 5' direction. As mentioned above, the methods involve a coupling step and a deprotection and oxidative step that can be repeated in an iterative manner to produce the target polynucleotide of interest.

Figure 2:
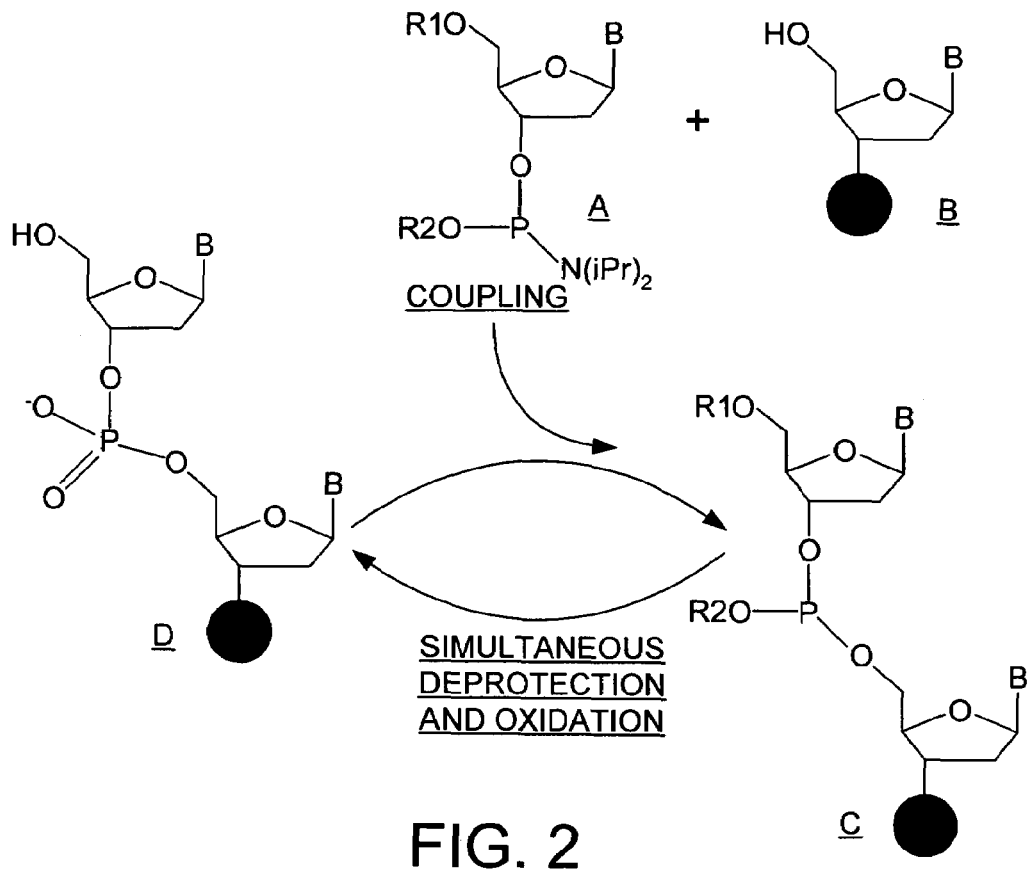
FIG. 2 schematically illustrates an embodiment of the two-step polynucleotide/oligonucleotide synthesis method in the 5' to 3' direction.

FIG. 2 schematically illustrates an embodiment of the two-step target polynucleotide synthesis method in the 5' to 3' direction under typical conditions. Structure A is provided and coupled with Structure B to form Structure C. The "B" moiety includes purine and pyrimidine bases and analogs thereof. "R1" can include groups such as, but not limited to, substituted carbonyls, substituted silanes and functional groups such as, carbonate, ester, amide, carbamate, silane, siloxane, orthoester, acetal, ketal, and the like. In particular, "R1" can include groups such as, but not limited to, oxycarbonate, aryl ester, alkyl ester, alkyl silane, aryl silane, alkylsiloxane, arylsiloxane, alkylarylsilane, and alkylarylsiloxane. Further, "R1" can include, but is not limited to, aryloxycarbonyl (Arco), methylthiophenyloxycarbonyl, flurormethylthiophenyloxycarbonyl, methoxymethylthiobenzylcarbonyl, dimethylthiophenylcarbonyl, acetylsalicylate, diacetylphenoxysalicylate, methylthioacetylsalicylate, dimethylthioacetylsalicylate, nitroacetylsalicylate, fluoroacetylsalicylate, cyclododecyloxydi(trimethoxysilyl)siloxane, diphenylmethoxydi(trimethoxysilyl)siloxane, and the like. "R2" can include groups such as, but not limited to, benzyl, substituted benzyl, phenyl, substituted phenol, tertiary alkyl, substituted tertiary alkyl, and the like. In particular, "R2" can include groups such as, but not limited to, alkylbenzyl, dialkylbenzyl, trialkylbenzyl, thioalkylbenzyl, phenylthiobenzyl, dithioalkylbenzyl, trithioalkylbenzyl, thioalkylhalobenzyl, alkyloxybenzyl, dialkyloxybenzyl, halobenzyl, dihalobenzyl, trihalobenzyl, esterifiedsalicyl, and the like. Further, "R2" can include, but is not limited to, 2-methoxybenzyl, methylthiophenyloxycarbonyl, flurormethylthiophenyloxycarbonyl, methoxymethylthiobenzylcarbonyl, dimethylthiophenylcarbonyl, acetylsalicyl, diacetylphenoxysalicyl, methylthioacetylsalicyl, dimethylthioacetylsalicyl, nitroacetylsalicyl, fluoroacetylsalicyl, and the like.

Structure C is oxidized and deprotected simultaneously or substantially simultaneously in an aqueous buffer solution to form Structure D. The aqueous buffer solution includes a compound or compound mixture that acts as both an oxidant and a nucleophile at a pH of about 6 to 10, about 6.5 to 8.5, about 6.5 to 8, and about 7 to 8. This mixture can include oxidizing agents that act as nucleophiles such as, but not limited to, hydroperoxides or peracids or mixtures of oxidizing agent that do and do not act as nucleophiles such as, but not limited to, mixtures of peroxides and peracids. The aqueous buffer solution includes compounds that have a pKa from about 1 to 11, about 3 to 11, about 7 to 11. The aqueous buffer solution includes compounds such as, but not limited to, hydrogen peroxide; peracids; performic acid; peracetic acid; perbenzoic acid; chloroperbenzoic acid, and the like; hydroperoxides; butylhydroperoxide; benzylhydroperoxide; phenylhydroperoxide; other similar compounds; and combinations thereof.

In addition, the aqueous buffer solution includes a buffer such as, but not limited to, tris(hydroxymethyl)aminomethane, aminomethylpropanol, citric acid, N,N'-bis(2-hydroxyethyl)glycine, 2-[bis(2-hydroxyethyl)amino]-2-(hydroxy-methyl)-1,3-propanediol, 2-(cyclohexylamino)ethane-2-sulfonic acid, N-2-hydroxyethyl)piperazine-N'-2-ethane sulfonic acid, N-(2-hydroxyethyl)piperazine-N'-3-propane sulfonic acid, morpholinoethane sulfonic acid, morpholinopropane sulfonic acid, piperazine-N,N'-bis(2-ethane sulfonic acid), N-tris(hydroxymethyl)methyl-3-aminopropane sulfonic acid, N-tris(hydroxymethyl)methyl-2-aminoethane sulfonic acid, N-tris(hydroxymethyl)methylglycine, and combinations thereof.

The hydrogen peroxide, peracids, and hydroperoxides are typically less than 30% weight/vol, more typically between 0.1% and 10% weight/vol and most typically 1% to 5% weight/vol.

The deprotection and oxidation occur substantially simultaneously or simultaneously, in other words both reactions are occurring at the same time. The rate of the two reactions can be different and therefore the competition times can be different. In the case of certain reactions, oxidation of a protecting group can result in enhanced rates of deprotection. It is most desirable if the deprotection reaction is substantially irreversible or irreversible. Although not intending to be bound by theory, the substantially irreversible nature of the reaction is due, at least in part, because the "R1" group breaks apart into three complexes, which substantially decrease the chance of a reverse reaction to reform "R1". Irreversibility is a desireable property of most if not all protecting groups and is equally desirable for R2.

Figure 3:
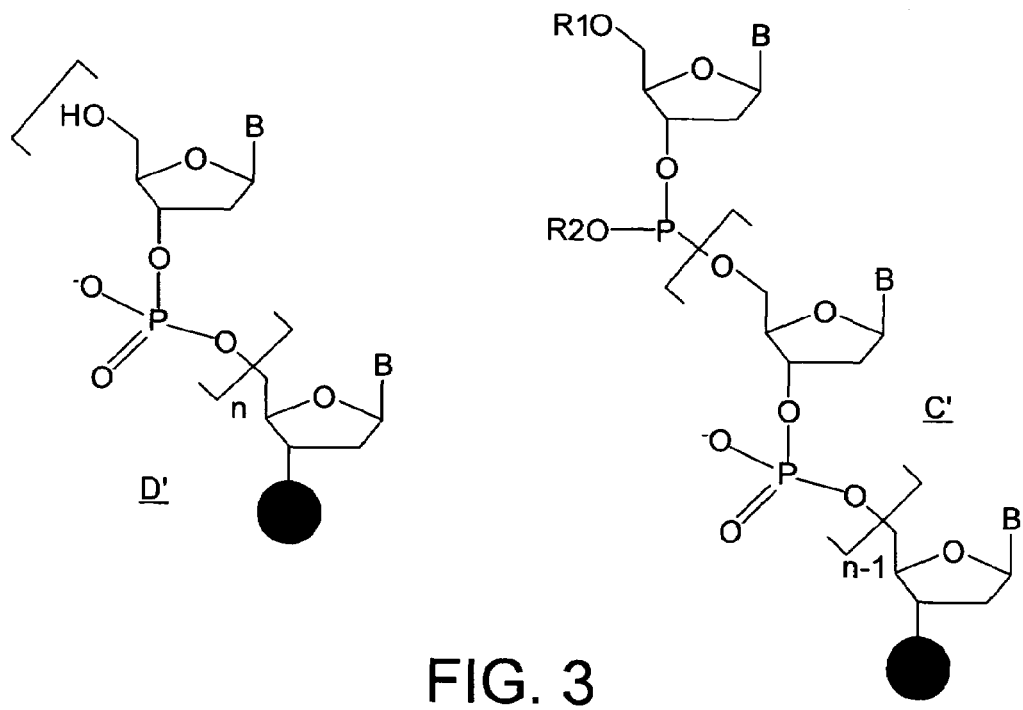
FIG. 3 illustrates embodiments of structures produced in the synthesis described in FIG. 2.

The two-step process can be repeated in an iterative manner by replacing Structure B with the reaction product produced after each deprotection and oxidation step. For example, Structure D is coupled with Structure A. FIG. 3 illustrates embodiments of Structure C' and Structure D', which represent structures that could be produced in an iterative manner using the method described in FIG. 2. "n" can be 1 to 350, 5 to 150, and 15 to 100, and depends on the length of the target polynucleotide to be synthesized.

The chemical synthesis method described herein is advantageous, in that the growing nucleic acid chain is exposed to fewer reagents and the synthesis cycle can be performed using simpler automation than with standard processes. When growing oligonucleotides are exposed to fewer chemical reagents, there are fewer chances of undesired chemical modifications, and those chemical modifications can be more easily controlled. As a manufacturing issue, simple automation can result in a more robust and reproducible manufacturing process. The non-reversible nature of the reactions is especially advantageous for synthesis on microscale and on planar surfaces. With highly reversible reactions it can be very difficult to achieve reaction completion under these conditions. The reactions are typically carried out under more stringent conditions to completely remove the reagent byproducts from the surface.

Figure 4:
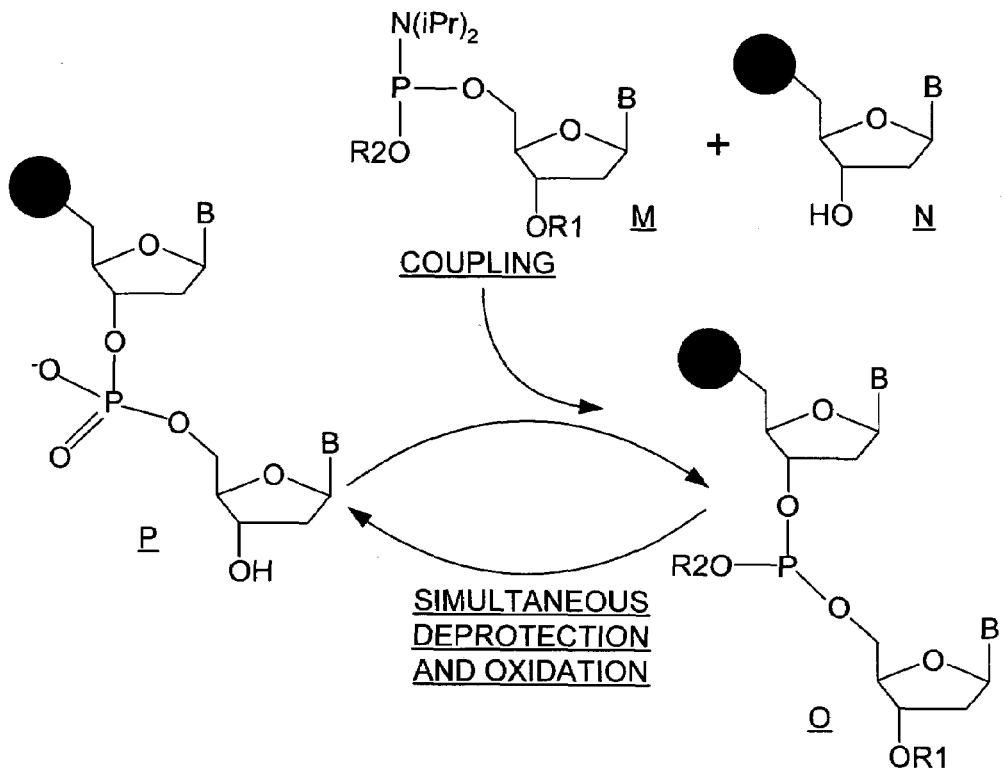
FIG. 4 schematically illustrates another embodiment of the two-step polynucleotide/oligonucleotide synthesis method in the 3' to 5' direction.

FIG. 4 schematically illustrates an embodiment of the two-step target polynucleotide synthesis method in the 3' to 5' direction under typical conditions. Structure M is provided and coupled with Structure N to form Structure O. "B", R1, and R2 are the same as those described in reference to FIG. 2 and the corresponding text.

Structure O is oxidized and deprotected simultaneously or substantially simultaneously in an aqueous buffer solution to form Structure P. The aqueous buffer solution is the same as that described in reference to FIG. 2 and the corresponding text.

In addition, the aqueous buffer solution includes a buffer as described above.

Figure 5:
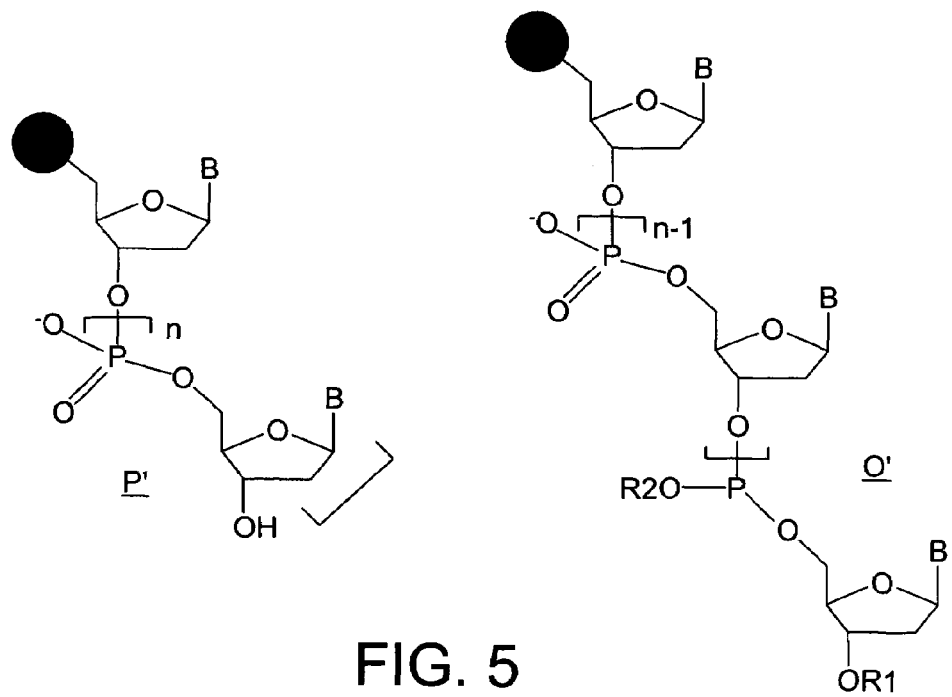
FIG. 5 illustrates embodiments of structures produced in the synthesis described in FIG. 2.

The two-step process can be repeated in an iterative manner by replacing Structure N with the reaction product produced after each deprotection and oxidation step. For example, Structure P is coupled with Structure M. FIG. 5 illustrates embodiments of Structure O' and Structure P', which represent structures that could be produced in an iterative manner using the method described in FIG. 4. "n" can be 1 to 350, 5 to 150, and 15 to 100, and depends on the length of the target polynucleotide to be synthesized.

As mentioned above, embodiments of the methods lend themselves to synthesis of polynucleotides on array substrates in either the 3'-to-5' or the 5'-to-3' direction. In the former case, the initial step of the synthetic process involves attachment of an initial nucleoside to the array substrate at the 3' position, leaving the 5' position available for covalent binding of a subsequent monomer. In the latter case, the initial step of the synthetic process involves attachment of an initial nucleoside to the array substrate at the 5' position, leaving the 3' position available for covalent binding of a subsequent monomer. Following synthesis, the polynucleotide may, if desired, be cleaved from the solid support. The details of the synthesis in either the 3'-to-5' or the 5'-to-3' direction will be readily apparent to the practitioner of ordinary skill, based on the prior art and the disclosure contained herein.

In addition, embodiments of the present disclosure provide methods of generating addressable arrays of polynucleotides on a substrate. Embodiments of this method include a solution having at least one of a nucleoside, a nucleotide, an oligonucleotide, or a polynucleotide, that is contacted with an array substrate to form a an oligonucleotide or a polynucleotide, and in an iterative manner, the target polynucleotide of interest can be fabricated according to and using one or more methods and nucleotide compounds as described herein.

In one such embodiment, at each of the multiple different addresses on the substrate (e.g., at least one hundred, at least one thousand, or at least ten thousand addresses), the in situ synthesis cycle is repeated so as to form the addressable array with the same or different polynucleotide sequences at one or more different addresses on the substrate. In the array forming method, the compounds to be coupled at respective addresses are deposited as droplets at those addresses using, for example, an inkjet printing system. The polynucleotides can be produced by disposing solutions (e.g., selected from four solutions, each containing a different nucleotide) on particular addressable positions in a specific order in an iterative process according the methods described herein.

The disclosure also encompasses the formation of an internucleotide bond between two polynucleotides or oligonucleotides, or between a polynucleotide and an oligonucleotide, resulting in an extended polynucleotide immobilized on the array surface. In such case, one of the polynucleotides or oligonucleotides is dissolved in a solvent and target polynucleotides can be made according to the methods described herein.

The array may contain any number of features, generally including at least tens of features, usually at least hundreds, more usually thousands, and as many as a hundred thousand or more features. All of the features may be different, or some or all could be the same. Each feature carries a predetermined moiety or a predetermined mixture of moieties, such as a particular polynucleotide sequence or a predetermined mixture of polynucleotides. The features of the array may be arranged in any desired pattern (e.g., organized rows and columns of features, for example, a grid of features across the substrate surface); a series of curvilinear rows across the substrate surface (for example, a series of concentric circles or semi-circles of features), and the like. In embodiments where very small feature sizes are desired, the density of features on the substrate may range from at least about ten features per square centimeter, or at least about 35 features per square centimeter, or at least about 100 features per square centimeter, and up to about 1000 features per square centimeter, up to about 10,000 features per square centimeter, or up to 100,000 features per square centimeter. Each feature carries a predetermined nucleotide sequence (which includes the possibility of mixtures of nucleotide sequences).

In one embodiment, about 10 to 100 of such arrays can be fabricated on a single substrate (such as glass). In such embodiment, after the substrate has the polynucleotides on its surface, the substrate may be cut into substrate segments, each of which may carry one or two arrays. It will also be appreciated that there need not be any space separating arrays from one another. Where a pattern of arrays is desired, any of a variety of geometries may be constructed, including for example, organized rows and columns of arrays (for example, a grid of arrays, across the substrate surface), a series of curvilinear rows across the substrate surface (for example, a series of concentric circles or semi-circles of arrays), and the like.

The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 300 mm, usually about 4 mm to 150 mm, more usually about 4 mm to 125 mm; a width in the range about 4 mm to 300 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. The substrate surface onto which the polynucleotides are bound may be smooth or substantially planar, or have irregularities, such as depressions or elevations. The configuration of the array may be selected according to manufacturing, handling, and use considerations.

In array fabrication, the quantities of polynucleotide available are usually very small and expensive. Additionally, sample quantities available for testing are usually also very small and it is therefore desirable to simultaneously test the same sample against a large number of different probes on an array. Therefore, one embodiment of the invention provides for fabrication of arrays with large numbers of very small, closely spaced features. Arrays may be fabricated with features that may have widths (that is, diameter, for a round spot) in the range from a minimum of about 10 micrometers to a maximum of about 1.0 cm. In embodiments where very small spot sizes or feature sizes are desired, material can be deposited according to the invention in small spots whose width is in the range about 1.0 micrometer to 1.0 mm, usually about 5.0 micrometers to 0.5 mm, and more usually about 10 micrometers to 200 micrometers. Interfeature areas will typically (but not essentially) be present that do not carry any polynucleotide. It will be appreciated, though, that the interfeature areas could be of various sizes and configurations.

Suitable substrates may have a variety of forms and compositions and may derive from naturally occurring materials, naturally occurring materials that have been synthetically modified, or synthetic materials. Examples of suitable support materials include, but are not limited to, nitrocellulose, glasses, silicas, teflons, and metals (for example, gold, platinum, and the like). Suitable materials also include polymeric materials, including plastics (for example, polytetrafluoroethylene, polypropylene, polystyrene, polycarbonate, and blends thereof, and the like), polysaccharides such as agarose (e.g., that available commercially as Sepharose®, from Pharmacia) and dextran (e.g., those available commercially under the tradenames Sephadex® and Sephacyl®, also from Pharmacia), polyacrylamides, polystyrenes, polyvinyl alcohols, copolymers of hydroxyethyl methacrylate and methyl methacrylate, and the like.

While the foregoing embodiments have been set forth in considerable detail for the purpose of making a complete disclosure of the invention, it will be apparent to those of skill in the art that numerous changes may be made in such details without departing from the spirit and the principles of the disclosure. Accordingly, the disclosure should be limited only by the following claims.

All patents, patent applications, and publications mentioned herein are hereby incorporated by reference in their entireties.

What is claimed is:

1. A method of forming polynucleotides, comprising:
providing a structure X selected from

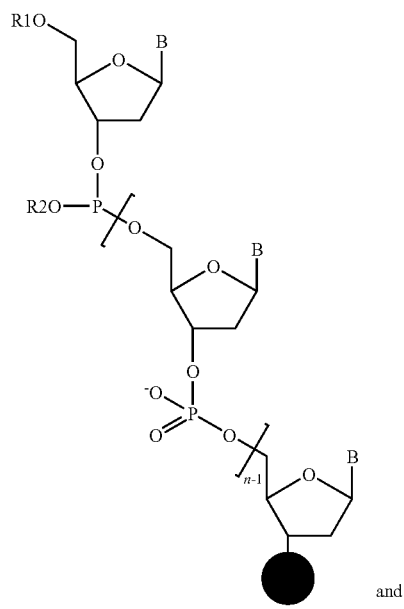

and

-continued

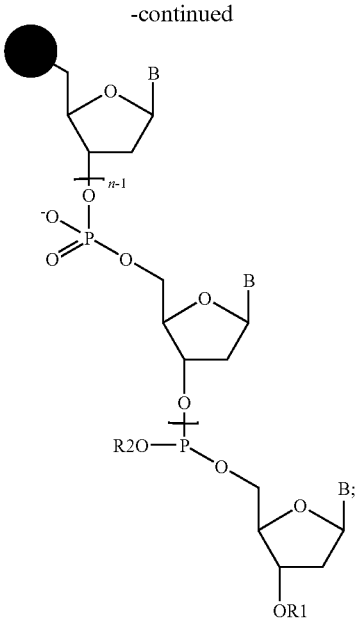

where R1 is selected from oxycarbonate, aryl ester, alkyl ester, alkyl silane, aryl silane, alkylsiloxane, arylsiloxane, alkylarylsilane, and alkylarylsiloxane and functional groups, where the functional group is selected from carbonate, ester, amide, carbamate, silane, siloxane, orthoester, acetal, and ketal;

where R2 is selected from benzyl, alkylbenzyl, dialkylbenzyl, trialkylbenzyl, thioalkylbenzyl, phenylthiobenzyl, dithioalkylbenzyl, trithioalkylbenzyl, thioalkylhalobenzyl, alkyloxybenzyl, dialkyloxybenzyl, halobenzyl, dihalobenzyl, trihalobenzyl, and esterified salicyl;

where B is optionally a purine or pyrimidine base or analog thereof;

wherein n is from 1 to 350; and wherein ● is a substrate; and oxidizing and deprotecting structure X simultaneously in an aqueous buffer solution, wherein the aqueous buffer solution comprises an oxidant and a nucleophile at a pH of about 6 to 10.

2. The method of claim 1, wherein the aqueous buffer solution is selected from hydrogen peroxide, peracids, performic acid, peracetic acid, perbenzoic acid, chloroperbenzoic acid, hydroperoxides, butylhydroperoxide, benzylhydroperoxide, phenylhydroperoxide, and combinations thereof.

3. The method of claim 1, wherein the aqueous buffer solution comprises hydrogen peroxide.

4. The method of claim 1, wherein R1 is selected from oxycarbonate, aryl ester, alkyl ester, alkyl silane, aryl silane, alkylsiloxane, arylsiloxane, alkylarylsilane, and alkylarylsiloxane, and wherein R2 is selected from alkylbenzyl, dialkylbenzyl, trialkylbenzyl, thioalkylbenzyl, phenylthiobenzyl, dithioalkylbenzyl, trithioalkylbenzyl, thioalkylhalobenzyl, alkyloxybenzyl, dialkyloxybenzyl, halobenzyl, dihalobenzyl, trihalobenzyl, and esterified salicyl.

5. The method of claim 1, wherein the pH of the aqueous buffer solution is about 6.5 to 8.5.

6. The method of claim 1, wherein the pH of the aqueous buffer solution is about 6.5 to 8.

7. The method of claim 1, wherein the pH of the aqueous buffer solution is about 7 to 8.

8. The method of claim 1, wherein oxidizing and deprotecting is an irreversible process.

9. The method of claim 1, wherein oxidizing and deprotecting produces a product selected from:

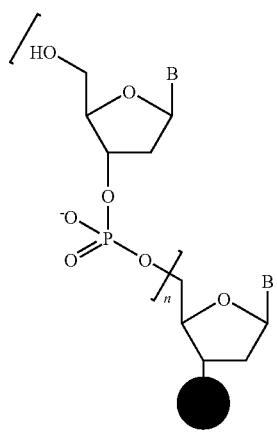

and

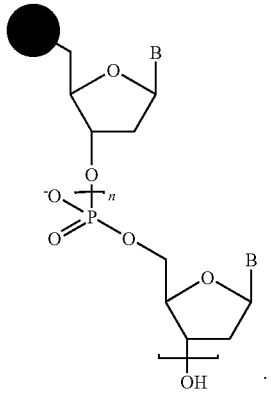

wherein n is from 2 to 350.

* * * * *

UNITED STATES PATENT AND TRADEMARK OFFICE
CERTIFICATE OF CORRECTION

PATENT NO. : 7,572,907 B2
APPLICATION NO. : 11/118599
DATED : August 11, 2009
INVENTOR(S) : Douglas J. Dellinger et al.

It is certified that error appears in the above-identified patent and that said Letters Patent is hereby corrected as shown below:

In column 12, lines 42-66, in Claim 1, delete " 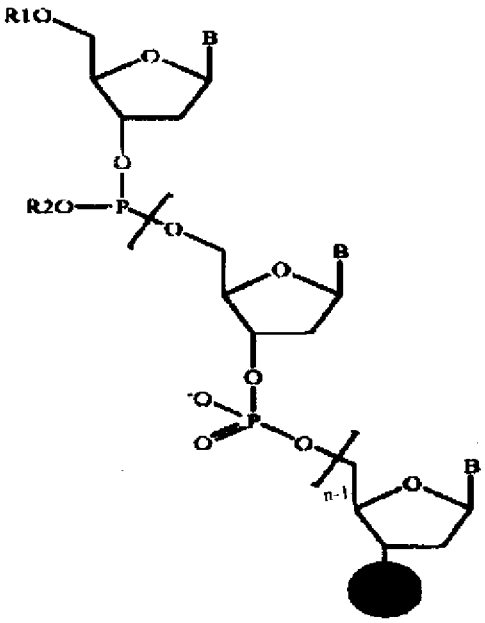  " and

Signed and Sealed this
Fourteenth Day of February, 2012

David J. Kappos
*Director of the United States Patent and Trademark Office* insert -- 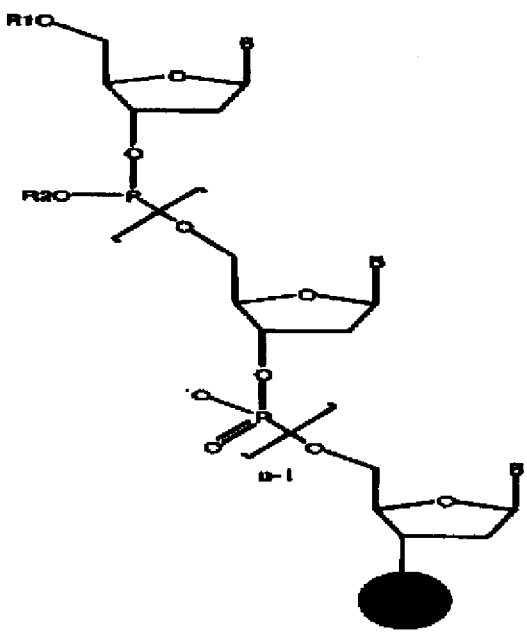 and --, therefor.
In column 13, lines 3-25, in Claim 1,
delete " 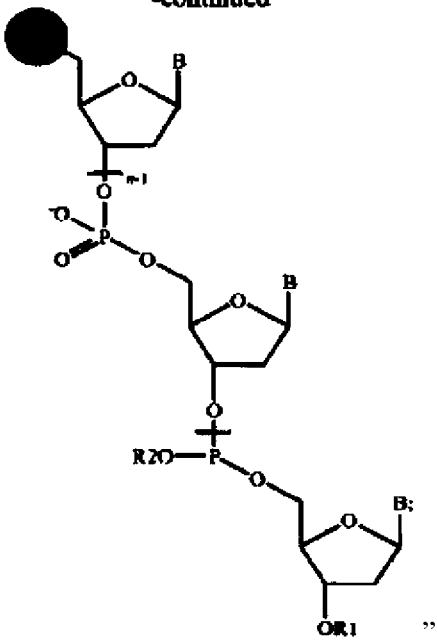 "

and insert -- 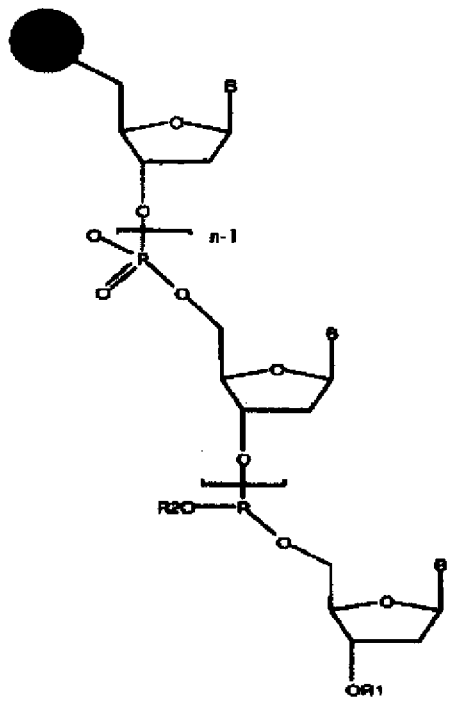 --, therefor.
In column 13, line 45, in Claim 1, delete "6to 10." and insert -- 6 to 10. --, therefor.
In column 14, lines 20-50, in Claim 9, delete " 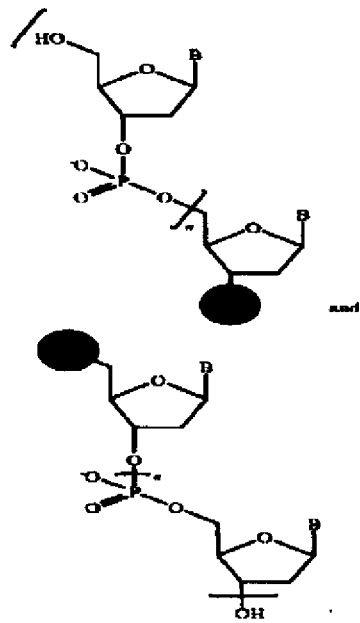 " and insert -- 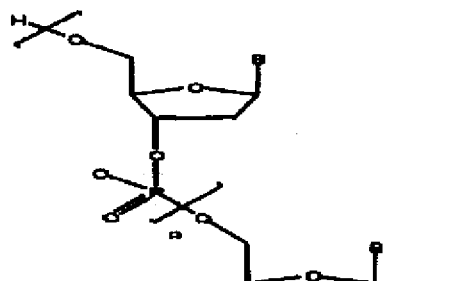 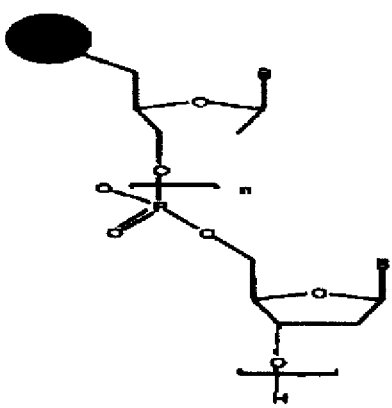 --, therefor.